(12) United States Patent
Chou et al.

(10) Patent No.: US 8,148,756 B2
(45) Date of Patent: Apr. 3, 2012

(54) SEPARATIVE EXTENDED GATE FIELD EFFECT TRANSISTOR BASED URIC ACID SENSING DEVICE, SYSTEM AND METHOD FOR FORMING THEREOF

(75) Inventors: Jung-Chuan Chou, Yunlin County (TW); Chih-Yu Lin, Taichung County (TW); Wei-Chuan Chen, Nantou County (TW); Cheng-Wei Chen, Tainan (TW)

(73) Assignee: National Yunlin University of Science and Technology, Yunlin (TW)

( * ) Notice: Subject to any disclaimer, the term of this patent is extended or adjusted under 35 U.S.C. 154(b) by 445 days.

(21) Appl. No.: 12/410,665

(22) Filed: Mar. 25, 2009

(65) Prior Publication Data

US 2009/0321792 A1    Dec. 31, 2009

(30) Foreign Application Priority Data

Jun. 30, 2008  (TW) .............................. 97124529 A

(51) Int. Cl.
*H01L 23/58* (2006.01)
*H01L 27/14* (2006.01)
(52) U.S. Cl. ........................................ 257/253; 257/414
(58) Field of Classification Search .................. 257/414, 257/253, E43.006, E51.016, E51.045; 438/49
See application file for complete search history.

(56) References Cited

U.S. PATENT DOCUMENTS

| | | | |
|---|---|---|---|
| 6,218,208 B1 * | 4/2001 | Chou et al. ..................... | 438/49 |
| 2006/0141474 A1 * | 6/2006 | Miyahara et al. ................ | 435/6 |
| 2008/0041721 A1 * | 2/2008 | Hsiung et al. ................. | 204/415 |

* cited by examiner

*Primary Examiner* — Hung Vu

(57) ABSTRACT

A separative extended gate field effect transistor based uric acid sensing device is provided, including: a substrate; a conductive layer including a silver paste layer on the substrate and a graphite-based paste layer on the silver paste layer; a conductive wire extended from the conductive layer; a titanium dioxide layer on the conductive layer; and a uric acid enzyme sensing film on the titanium dioxide layer.

16 Claims, 5 Drawing Sheets

SEPARATIVE EXTENDED GATE FIELD EFFECT TRANSISTOR BASED URIC ACID SENSING DEVICE, SYSTEM AND METHOD FOR FORMING THEREOF

CROSS REFERENCE TO RELATED APPLICATIONS

This Application claims priority of Taiwan Patent Application No. 097124529, filed on Jun. 30, 2008, the entirety of which is incorporated by reference herein.

BACKGROUND OF THE INVENTION

1. Field of the Invention

The present invention relates to a uric acid sensing device, and in particular relates to a separative extended gate field effect transistor based uric acid sensing device.

2. Description of the Related Art

Uric acid is one of the metabolism products of purine (one important constituent of a genetic material such as nucleic acid) and can be produced through autosynthesis, tissue dissolution and nucleoprotein ingestion by a human body. Purine is metabolized through the liver to form uric acid, and uric acid is metabolized to drain from the kidney. Uric acid concentrations in blood increase when the human body production rate is faster than the kidney draining rate. In the U.S.A., medical reports indicate that when uric acid concentrations in patients blood are over the standard concentration about 0.1 mg, morbidity of cardiopathy increases more than high cholesterol and hypertension. Additionally, when using a diuretic to cure hypertension, uric acid concentrations will increase for patients with higher than 0.1 mg of uric acid concentration in their blood. The high concentrations of uric acid and blood sugar in blood cause pathological symptoms for humans. Thus, a biosensor with high sensitivity, easy operation and real-time response to test concentrations of uric acid in blood has been developed.

An ion-sensitive field effect transistor (ISFET) is applied to an electrochemical sensing device. The structure of a separative extended gate field effect transistor (SEGFET) has been developed from the ISFET. In contrast with the ISFET using high impedance material as its sensing thin film, the ion sensing thin film of the SEGFET is fabricated by low impedance material for relatively better conductivity and sensitivity. Therefore, high impedance material is suitable for ISFETs, but not for SEGFETs. Meanwhile, the SEGFET structure comprises a MOSFET which retains a metal gate electrode and utilizes a signal wire to connect the separative ion sensing film and the field effect transistor.

In 1983, J. Van der Spiegel et al developed an extended gate chemical sensitive field effect transistor, which used a plane array structure, including four sensing parts deposited of different materials such as $IrO_x$, $LaF_3$, $AgCl$ and $Ag_2S$ to from the sensing thin films for detecting four kinds of ions, $H^+$, $F^-$, $Cl^-$ and $Ag^+$ (J. Van der Spiegel, I. Lauks, P. Chan D. Babic, 1983, "The extended gate chemical sensitive field effect transistor as multi-species microprobe", Sensors and Actuators B, Vol. 4, pp. 291-298).

BRIEF SUMMARY OF THE INVENTION

The invention provides a separative extended gate field effect transistor based uric acid sensing device, comprising: a substrate; a conductive layer comprising a silver paste layer on the substrate and a graphite-based paste layer on the silver paste layer; a conductive wire extended from the conductive layer; a titanium dioxide layer on the conductive layer; and a uric acid enzyme sensing film on the titanium dioxide layer.

The invention provides a separative extended gate field effect transistor based uric acid sensing system, comprising: the separative extended gate field effect transistor based uric acid sensing device mentioned above; a metal-oxide-semiconductor field effect transistor, wherein the separative extended gate field effect transistor based uric acid sensing device is connected to the metal-oxide-semiconductor field effect transistor by the conductive wire; a semiconductor parameter analyzer electrically connected to the metal-oxide-semiconductor field effect transistor; and a reference electrode electrically connected to the semiconductor parameter analyzers.

The invention also provides a separative extended gate field effect transistor based uric acid sensing system, comprising: the separative extended gate field effect transistor based uric acid sensing device mentioned above; an instrumentation amplifier, wherein the separative extended gate field effect transistor based uric acid sensing device is connected to the instrumentation amplifier by the conductive wire; a reference electrode electrically connected to the instrumentation amplifier; a high impedance digital meter electrically connected to the instrumentation amplifier; and a computer electrically connected to the high impedance digital meter, wherein the computer is used to analyze signals from the separative extended gate field effect transistor based uric acid sensing device and the reference electrode.

The invention further provides a method for forming a separative extended gate field effect transistor based uric acid sensing device, comprising: (a) providing a substrate; (b) forming a silver paste layer on the substrate; (c) forming a graphite-based paste layer on the silver paste layer, wherein the silver paste layer and the graphite-based paste layer constitute a conductive layer; (d) forming a conductive wire extended from the conductive layer; (e) forming a titanium dioxide layer on the conductive layer; and (f) forming a uric acid enzyme sensing film on the titanium dioxide layer.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Each component constituting the uric acid sensing device of the invention will be described in greater detail hereinafter. In this specification, expressions such as "overlying the substrate", "above the layer", or "on the film" simply denote a relative positional relationship with respect to the surface of the base layer, regardless of the existence of intermediate layers. Accordingly, these expressions may include not only the direct contact of layers, but also, non-contact state of one or more laminated layers.

Figure 1:
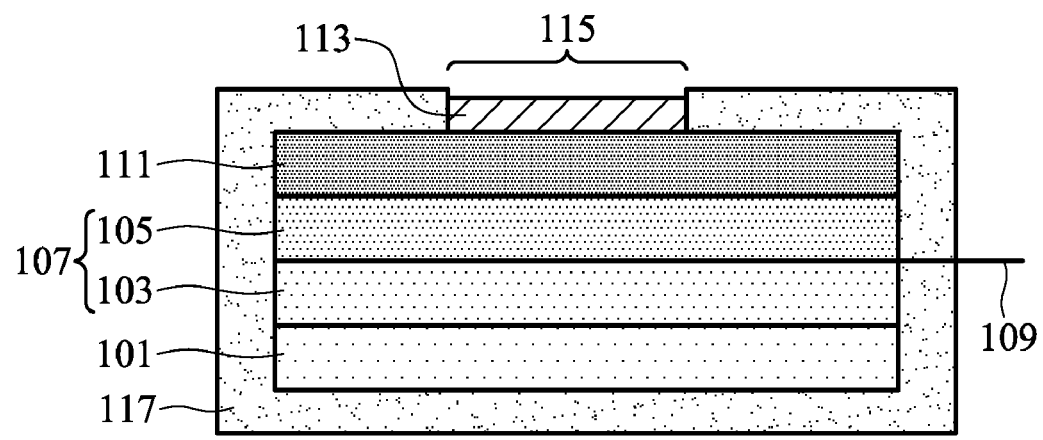
FIG. 1 shows a framework illustrating the separative extended gate field effect transistor based uric acid sensing device of the invention.
Figure 2:
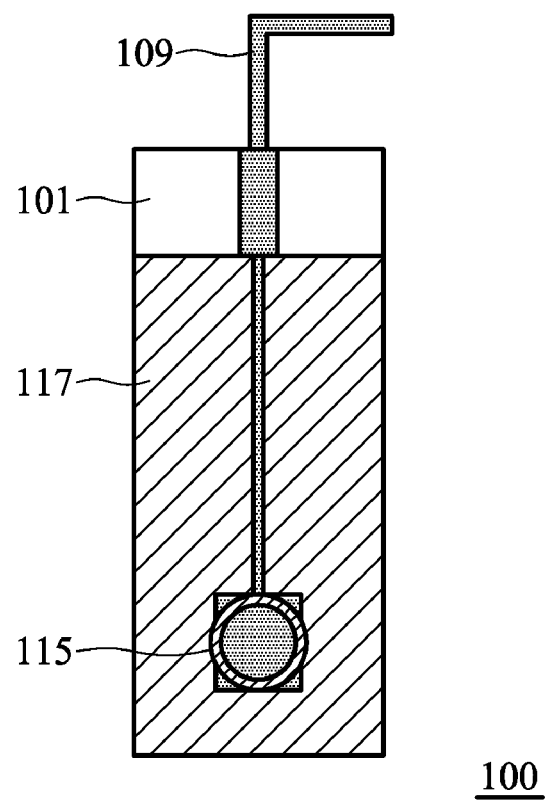
FIG. 2 is a schematic view of the separative extended gate field effect transistor based uric acid sensing device shown in FIG. 1.

The invention provides a method for forming a separative extended gate field effect transistor based uric acid sensing device. See FIG. 1 and FIG. 2. In one embodiment, the method for forming a separative extended gate field effect transistor based uric acid sensing device comprises first providing a substrate 101. The substrate 101 may comprises a flexible substrate, preferably a polyethylene terephthalate substrate (PET) substrate.

Then, a silver paste layer 103 is formed on the substrate 101 and a graphite-based paste layer 105 is formed on the silver paste layer 103, wherein the method for forming the silver paste layer 103 and the graphite-based paste layer 105 may comprise a screen printing process. The silver paste layer 103 and the graphite-based paste layer 105 constitute a conductive layer 107. After, a conductive wire 109 is formed extending from the conductive layer 107 for external contact thereto.

Next, a titanium dioxide layer 111 is formed on the conductive layer 107. The method for forming the titanium dioxide layer 111 may comprise a radio frequency sputtering process. A processing time for the radio frequency sputtering process is about 60-90 minutes, preferably 60 minutes. A target used in the radio frequency sputtering process comprises titanium dioxide target with purity of 99.99%, preferably greater than 99.99%. Moreover, power of the radio frequency sputtering process is about 100-150 W, preferably, 100 W. The processing pressure for the radio frequency sputtering process is about 25-35 mTorr, preferably, 30 mTorr. An argon gas flow for the process for forming the titanium dioxide layer 111 is about 35-50 sccm, preferably about 40 sccm, and an oxygen gas flow for the process for forming the titanium dioxide layer 111 is about 2-5 sccm, preferably about 2 sccm. In addition, a ratio of the argon gas flow to the oxygen gas flow is about 7/1-20/1.

Finally, a uric acid enzyme sensing film 113 is formed on the titanium dioxide layer 111 to complete the separative extended gate field effect transistor based uric acid sensing device of the invention 100. A method for forming the uric acid enzyme sensing film may comprise a covalent bonding process using enzyme immobilization technology. A carrier used in the covalent bonding process may comprise a 3-glycidoxypropyltrimethoxysilane (GPTS) solution and toluene, wherein volume ratio of the 3-glycidoxypropyltrimethoxysilane (GPTS) solution to the toluene is about 20:80. The mixture of the 3-glycidoxypropyltrimethoxysilane (GPTS) solution and toluene are dropped on the titanium dioxide layer 111. After the mixture of the 3-glycidoxypropyltrimethoxysilane (GPTS) solution and toluene is immobilized, a uric acid enzyme is dropped thereon to form the uric acid enzyme sensing film 113, wherein the uric acid enzyme may comprise uricase.

In addition, after the titanium dioxide layer 111 is formed, the substrate 101, the silver paste layer 103, the graphite-based paste layer 105 and titanium dioxide layer 111 may be further packaged with a package material and during the packaging process, an opening is left, and then the method for forming the uric acid enzyme sensing film 113 mentioned above is used to form the uric acid enzyme sensing film 113 in the opening to form a sensing window 115. Finally, completing the separative extended gate field effect transistor based uric acid sensing device of the invention 100. The package material may comprise a UV-cured paste. After packaging the device with the UV-cured paste, the UV-cured paste may be irradiated by a UV light to solidify the UV-cured paste to complete the packaging process.

The separative extended gate field effect transistor based uric acid sensing device of the invention 100 may further be combined with other devices to form a separative extended gate field effect transistor based uric acid sensing system 300 for measuring current versus voltage changes. Please see FIG. 3. The system may comprise the separative extended gate field effect transistor based uric acid sensing device of the invention 100, a metal-oxide-semiconductor field effect transistor 301, a semiconductor parameter analyzer 303 and a reference electrode 305. The conductive wire 109 of the sensing device 100 is connected to the metal-oxide-semiconductor field effect transistor 301, the metal-oxide-semiconductor field effect transistor 301 is electrically connected to the semiconductor parameter analyzer 303 and the reference electrode 305 is electrically connected to the semiconductor parameter analyzer 303. The reference electrode 305 may comprise an Ag/AgCl reference electrode.

Furthermore, sensitivity of the separative extended gate field effect transistor based uric acid sensing system 300 mentioned above may be about 40-60 mV/pH, preferably 45.35 mV/pH, and the sensing range thereof is about pH 1-9.

The separative extended gate field effect transistor based uric acid sensing device of the invention 100 may further be combined with other devices to form a separative extended gate field effect transistor based uric acid sensing system 400 for measuring the voltage versus time changes. Please see FIG. 4. The system may comprise the separative extended gate field effect transistor based uric acid sensing device of the invention 100, an instrumentation amplifier 401, a reference electrode 305, a high impedance digital meter 403 and a computer 405. The conductive wire 109 of the sensing device 100 is connected to the instrumentation amplifier 401, and the reference electrode 305 is electrically connected to the instrumentation amplifier 401. The instrumentation amplifier 401 is electrically connected to the high impedance digital meter 403 and the high impedance digital meter 403 is electrically connected to the computer 405, wherein the computer 405 is used to analyze signals from the separative extended gate field effect transistor based uric acid sensing device 100 and the reference electrode 305. The reference electrode 305 may comprise an Ag/AgCl reference electrode.

EXAMPLE

Preparation of the Uric Acid Sensing Device
1. Preparation of the Conductive Layer
(1) A polyethylene terephthalate substrate was provided.
(2) A silver paste layer was prepared by a screen printing machine and a 20 μm in thickness silver paste layer was attached on the polyethylene terephthalate substrate and then placed in a oven at 100° C. for 15 minutes for solidification.
(3) A graphite-based paste layer was prepared by a screen printing machine and a 20 μm in thickness graphite-based paste layer was attached on the silver paste layer and then placed in a oven at 100° C. for 15 minutes for solidification.
2. Preparation of the Titanium Dioxide Layer In the invention, a radio frequency sputtering process was used to form the titanium dioxide layer and the process parameters used in the radio frequency sputtering process are described in the following:

(1) The power of the radio frequency sputtering process was 100 W when preparing the titanium dioxide layer;

(2) The processing pressure was 30 mTorr;

(3) The titanium dioxide target was with purity of 99.99%;

(4) The argon gas flow for the process for forming the titanium dioxide layer was 40 sccm;

(5) The oxygen gas flow for the process for forming the titanium dioxide layer was 2 sccm;

(6) The processing time for the radio frequency sputtering process was 60 minutes.

3. Packaging Process

After preparation of the titanium dioxide layer was completed, the device was packaged with a UV cured paste using a screen printing process. The deposition thickness of the UV-cured paste was 50 μm, and a 1.5 mm opening in width and a position for the conductive wire to extend from the conductive layer were left unpackaged. Next, the device was placed under a UV light for about 40 seconds for solidifying the UV-cured paste to protect the device.

4. Preparation of the Uric Acid Enzyme Sensing Film

The uric acid enzyme sensing film was formed by an enzyme immobilization method with 3-glycidoxypropyltrimethoxysilane (GPTS) (Y. Shindo, N. Katagirl, T. Ebisuno, M. Hasegawa and M. Misuda, 1996, "Network Formation and Swelling Behavior of Photosensitive Poly(vinyl alcohol) Gels Prepared by Photogenerated Crosslinking", Angewandte Makromolekulare Chemie, Vol. 240, PP. 231-239). The method for preparing the uric acid enzyme sensing film is described in the following:

(1) A mixture of 3-glycidoxypropyltrimethoxysilane and toluene was prepared, wherein the volume ratio of the 3-glycidoxypropyltrimethoxysilane (GPTS) solution to the toluene was about 20:80. After the mixture was oscillated by an ultrasonic cleaner, 2 μl of the 3-glycidoxypropyltrimethoxysilane and toluene was dropped on the surface of the titanium dioxide layer in the unpackaged opening, and placed in an oven at 100° C. for 1 hour. After, the device was placed in a PBS buffer (20 mM, pH 7.0) for about 5 minutes to remove the un-immobilized mixture of 3-glycidoxypropyltrimethoxysilane and toluene.

(2) 5 mg of uricase was added into 50 ml of a PBS buffer (20 mM, pH 7.0) and mixed to obtain a uricase solution.

(3) 2 μl of the uricase solution was dropped in the sensing window (opening) which completed the immobilization of the mixture of 3-glycidoxypropyltrimethoxysilane and toluene, and then placed in a refrigerator for 12 hours.

Before using the device to measure sample solutions, the device was dipped into a PBS buffer (20 mM, pH 7.0) for about 5 minutes to remove the un-immobilized enzymes and then the uric acid sensing device was completed.

Preparation of the Sample Solutions

1. Preparation of the PBS Buffer

When preparing the sample solutions, the PBS solution was used as a buffer to prevent the pH value of the sample solutions to change acutely when the sample solutions were diluted or added a trace of acid or base to help study the features of the sensing device of the invention. The method for preparing of the PBS buffer is described in the following:

(1) 136.09 mg of $KH_2PO_4$ and 50 ml of deionized water were mixed to obtain a $KH_2PO_4$ buffer (20 mM, pH 4.1);

(2) 174.18 mg of $K_2HPO_4$ and 50 ml of deionized water were mixed to obtain a $K_2HPO_4$ buffer (20 mM, pH 9.08);

(3) The $KH_2PO_4$ buffer and the $K_2HPO_4$ buffer were well mixed and measured by a pH meter to obtain a pH value thereof and then a PBS buffer was obtained. The PBS buffer was used to prepare the uric acid sample solutions.

2. Preparation of the Uric Acid Sample Solutions

The uric acid sample solutions were prepared by adding an appropriate amount of uric acid into the PBS buffer. Using different amounts of uric acid and PBS buffer may result in obtaining uric acid sample solutions with different uric acid concentrations, different phosphate concentrations or different pH values. The concentrations of the uric acid sample solutions were 2-10 mg/dL and the pH value of the uric acid sample solutions were pH 7. The method for preparing of the uric acid sample solutions is described in the following:

(1) 10 mg/dL of a uric acid sample solution was prepared. 50 mg of uric acid was added into 500 ml of PBS buffer and well mixed to obtain 10 mg/dL of a uric acid sample solution (solution A).

(2) 8 mg/dL of a uric acid sample solution was prepared. 10 ml of PBS buffer and 40 ml of solution A were well mixed to obtain 8 mg/dL of a uric acid sample solution.

(3) 6 mg/dL of uric acid sample solution was prepared. 20 ml of PBS buffer and 30 ml of solution A were well mixed to obtain 6 mg/dL of a uric acid sample solution.

(4) 4 mg/dL of uric acid sample solution was prepared. 30 ml of PBS buffer and 20 ml of solution A were well mixed to obtain 4 mg/dL of a uric acid sample solution.

(5) 2 mg/dL of uric acid sample solution was prepared. 40 ml of PBS buffer and 10 ml of solution A were well mixed to obtain 2 mg/dL of a uric acid sample solution.

(6) The PBS buffer and uric acid sample solutions were stored at a low temperature (5-10° C.) and prevented from being influenced by sun light and high temperatures.

Current-Voltage (I-V) Measuring System and Sample Solutions Measurement

Figure 3:
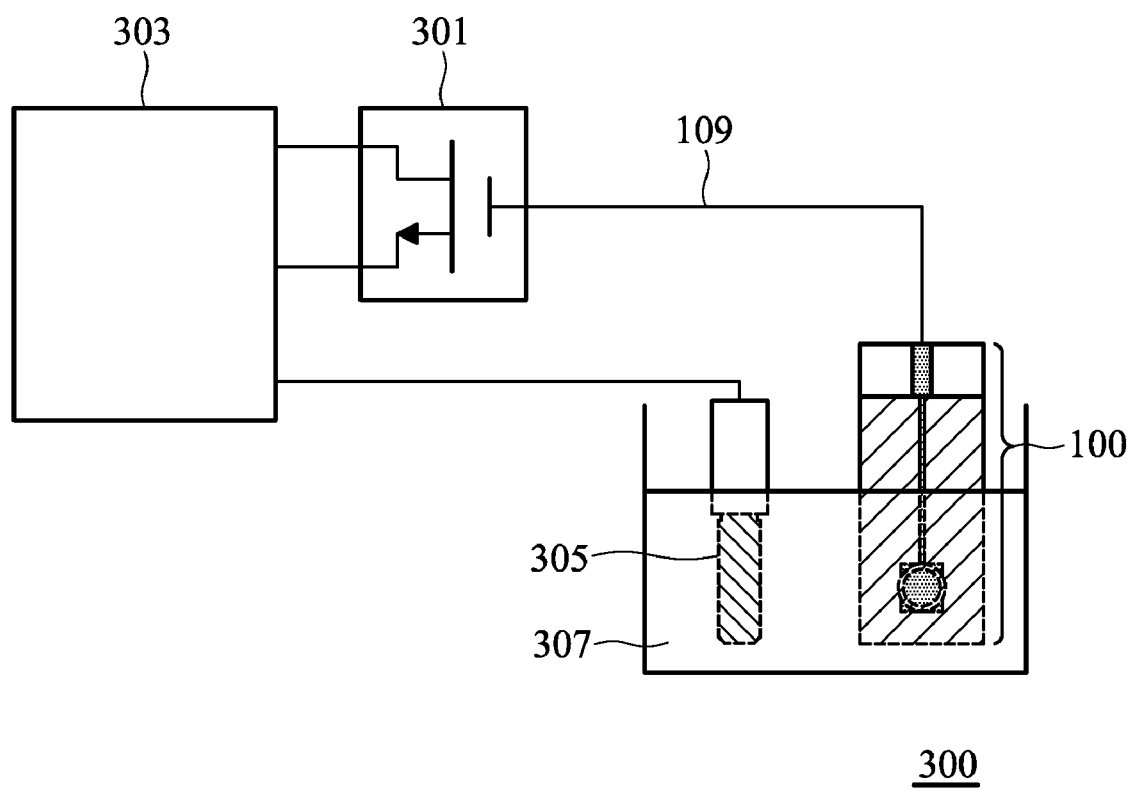
FIG. 3 shows a current versus voltage measuring system of the invention.
Figure 5:
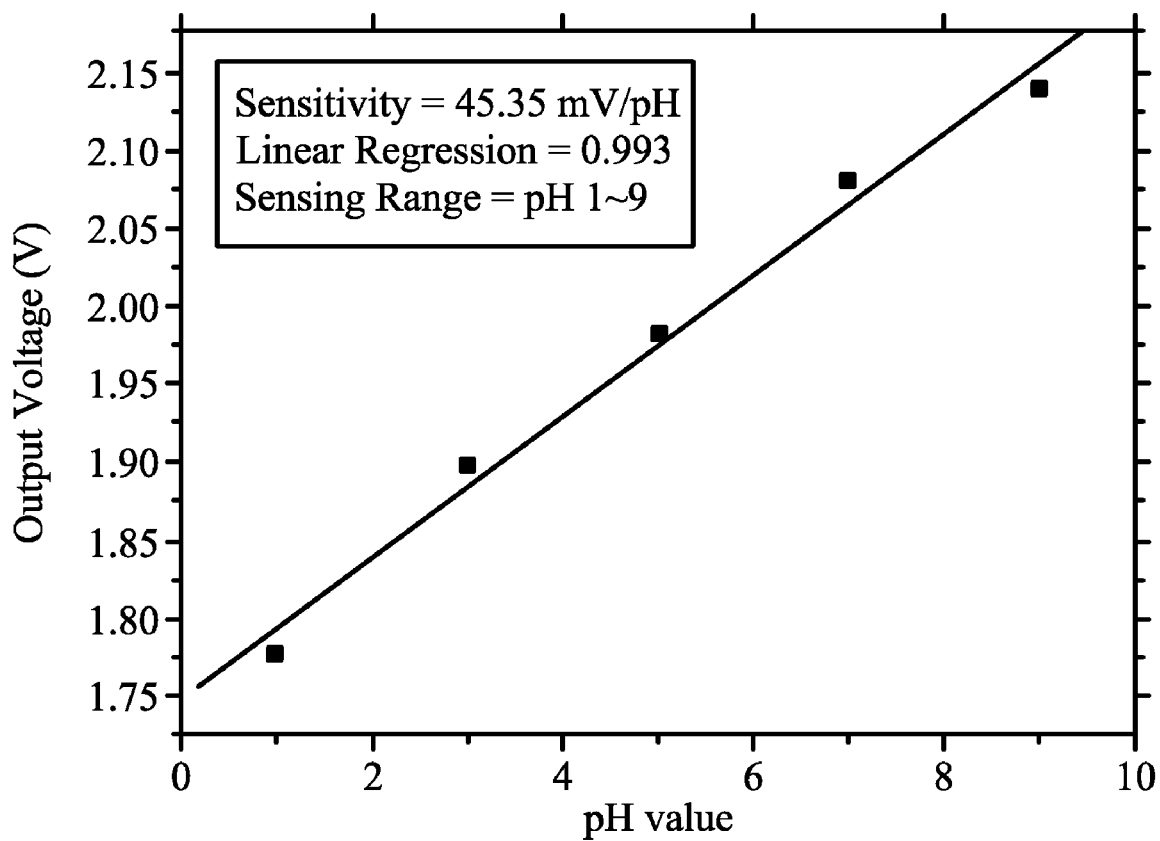
FIG. 5 shows curves for the sensitivity and the linearity of the separative extended gate field effect transistor based uric acid sensing device of the invention.

The current-voltage (I-V) measuring system of the invention 300 is shown in FIG. 3 and the system was used to analyze the response voltages corresponding to different pH value degree changes to realize the sensitivity and the linear regression of the uric acid sensing device of the invention. By using a commercial metal-oxide-semiconductor field effect transistor and an Ag/AgCl reference electrode connected to a test-lead converter box and a semiconductor parameter analyzer 305 (Keithley 236), a stable electric potential was provided for the reference electrode 305 in the sample solution 307 and the metal-oxide-semiconductor field effect transistor was able to operate in the linear region. Due to the circuitry of the system, the sensitivity and the linear regression of the uric acid sensing device of the invention were obtained. As shown in FIG. 5, the sensitivity and the linear regression of the uric acid sensing device were 45.35 mV/pH and 0.993, respectively. The results showed that the sensitivity of the uric acid sensing device of the invention was better than the sensitivity of 36.49 mV/pH of the sensing device in Chou et al (Jung Chuan Chou, Hung-Hsi Yang, 2006, "Study the Characteristics of Titanium Oxide Hydrogen Ion Sensor Using XRD and AES", Rare Metal Materials and Engineering, Vol. 35, PP. 250-251).

Voltage-Time (V-T) Measuring System and Sample Solutions Measurements

Figure 4:
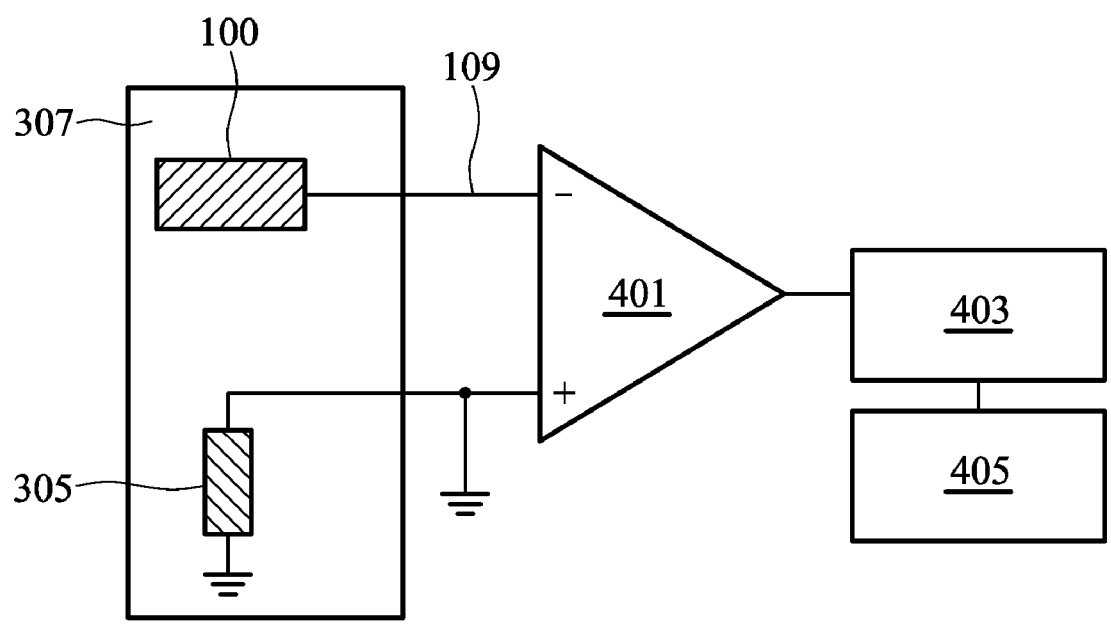
FIG. 4 shows a voltage versus time measuring system of the invention.
Figure 6:
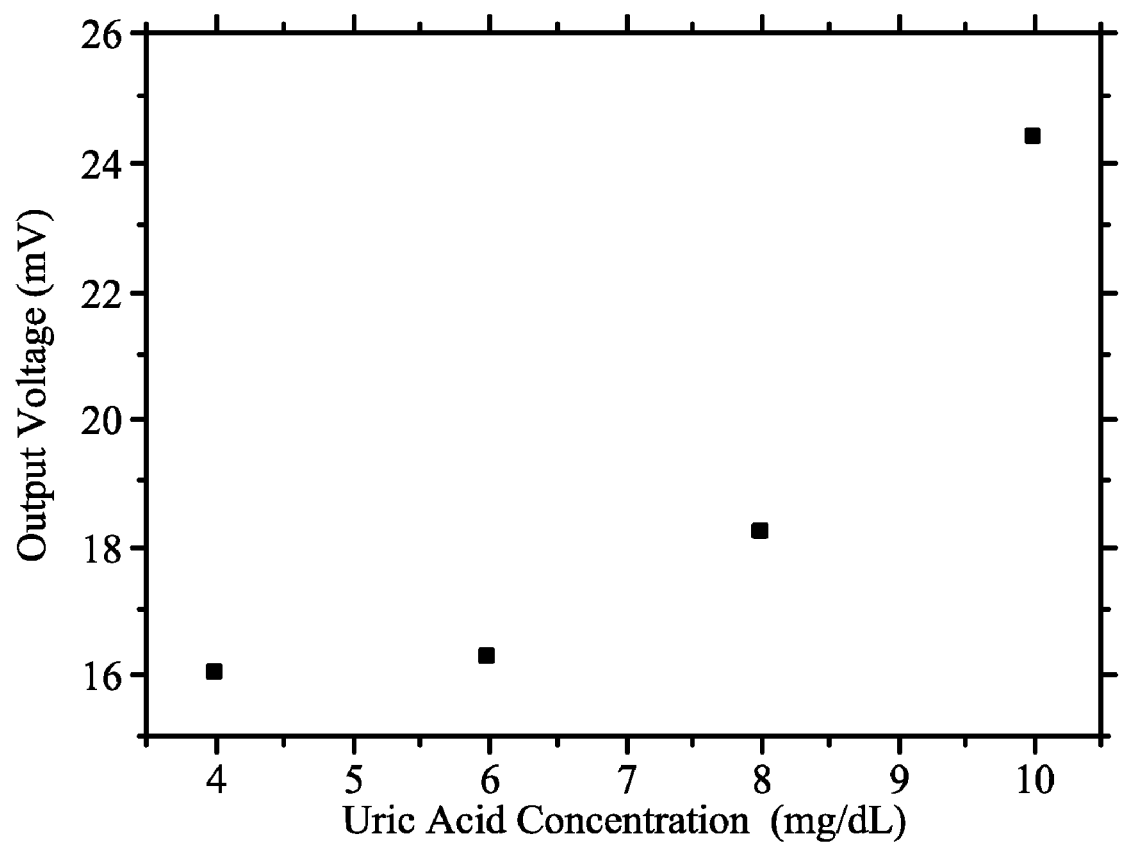
FIG. 6 shows response voltages obtained through measuring the uric acid sample solutions with different concentrations with the separative extended gate field effect transistor based uric acid sensing device of the invention.

As shown in FIG. 4, measuring data was recoded by the voltage-time (V-T) measuring system, by utilizing the instrumentation amplifier 401 (LT1167) with a control program (HP VEE program) to connect to the high impedance digital meter 403 (HP 34401A) and the computer 405. The instrumentation amplifier 401 was used as a front-end detective circuit of the uric acid sensing device of the invention. Moreover, the uric acid sensing device 100 was dipped in the uric acid sample solutions 307 with different concentrations prepared by the method mentioned above and the output response voltages for the uric acid sensing device 100 dipped in the uric acid sample solutions with different concentrations were recorded one by one. As shown in FIG. 6, when the concentration of the uric acid sample solution changed from 4 mg/dL to 10 mg/dL, the output response voltage curve tended to be linear. Thus, the results showed that when the concentration of the uric acid sample solution increased, the redox reaction ability for the uric acid sensing film increased and the voltage responsiveness of the uric acid sensing film was raised.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for forming a separative extended gate field effect transistor based uric acid sensing device, comprising:
   (a) providing a substrate;
   (b) forming a silver paste layer on the substrate;
   (c) forming a graphite-based paste layer on the silver paste layer, wherein the silver paste layer and the graphite-based paste layer constitute a conductive layer;
   (d) forming a conductive wire extended from the conductive layer;
   (e) forming a titanium dioxide layer on the conductive layer; and
   (f) forming a uric acid enzyme sensing film on the titanium dioxide layer.

2. The method for forming a separative extended gate field effect transistor based uric acid sensing device as claimed in claim 1, wherein the substrate comprises a flexible substrate.

3. The method for forming a separative extended gate field effect transistor based uric acid sensing device as claimed in claim 2, wherein the flexible substrate comprises a polyethylene terephthalate substrate.

4. The method for forming a separative extended gate field effect transistor based uric acid sensing device as claimed in claim 1, wherein a method for forming the silver paste layer comprises a screen printing process.

5. The method for forming a separative extended gate field effect transistor based uric acid sensing device as claimed in claim 1, wherein a method for forming the graphite-based paste layer comprises a screen printing process.

6. The method for forming a separative extended gate field effect transistor based uric acid sensing device as claimed in claim 1, wherein a method for forming the titanium dioxide layer comprises a radio frequency sputtering process.

7. The method for forming a separative extended gate field effect transistor based uric acid sensing device as claimed in claim 6, wherein a processing time for the radio frequency sputtering process is about 60-90 minutes.

8. The method for forming a separative extended gate field effect transistor based uric acid sensing device as claimed in claim 7, wherein a target used in the radio frequency sputtering process comprises titanium dioxide target with purity of 99.99%.

9. The method for forming a separative extended gate field effect transistor based uric acid sensing device as claimed in claim 7, wherein power of the radio frequency sputtering process is about 100-150 W.

10. The method for forming a separative extended gate field effect transistor based uric acid sensing device as claimed in claim 7, wherein a processing pressure for the radio frequency sputtering process is about 25-35 mTorr.

11. The method for forming a separative extended gate field effect transistor based uric acid sensing device as claimed in claim 7, wherein an argon gas flow and an oxygen gas flow for the process for forming the titanium dioxide layer are about 35-50 sccm and 2-5 sccm, respectively.

12. The method for forming a separative extended gate field effect transistor based uric acid sensing device as claimed in claim 11, wherein a ratio of the argon gas flow to the oxygen gas flow is about 7/1-20/1.

13. The method for forming a separative extended gate field effect transistor based uric acid sensing device as claimed in claim 1, wherein a uric acid enzyme contained in the uric acid enzyme sensing film comprises uricase.

14. The method for forming a separative extended gate field effect transistor based uric acid sensing device as claimed in claim 1, wherein a method for forming the uric acid enzyme sensing film comprises a covalent bonding process using enzyme immobilization technology.

15. The method for forming a separative extended gate field effect transistor based uric acid sensing device as claimed in claim 14, wherein a carrier used in the covalent bonding process comprises a 3-glycidoxypropyltrimethoxysilane (GPTS) solution and toluene.

16. The method for forming a separative extended gate field effect transistor based uric acid sensing device as claimed in claim 15, wherein a volume ratio of the 3-glycidoxypropyltrimethoxysilane (GPTS) solution to the toluene is about 20:80.

* * * * *